United States Patent [19]

Breipohl et al.

[11] Patent Number: 5,124,478

[45] Date of Patent: Jun. 23, 1992

[54] ACID-LABILE ANCHOR GROUPS FOR THE SYNTHESIS OF PEPTIDE AMIDES BY A SOLID-PHASE METHOD

[75] Inventors: Gerhard Breipohl, Frankfurt am Main; Jochen Knolle, Kriftel; Werner Stüber, Lahntal, all of Fed. Rep. of Germany

[73] Assignee: Hoechst Aktiengesellschaft, Frankfurt am Main, Fed. Rep. of Germany

[21] Appl. No.: 287,213

[22] Filed: Dec. 20, 1988

[30] Foreign Application Priority Data

Dec. 22, 1987 [DE] Fed. Rep. of Germany ....... 3743620
Jun. 1, 1988 [DE] Fed. Rep. of Germany ....... 3818576

[51] Int. Cl.$^5$ .................................. C07C 229/38
[52] U.S. Cl. .................................. 562/441; 530/337; 562/451; 562/460; 562/468; 560/42; 560/52; 560/57
[58] Field of Search ............... 530/337; 562/451, 460, 562/468, 441; 560/42, 52, 57

[56] References Cited

U.S. PATENT DOCUMENTS

4,922,015  5/1990  Breipohl et al. .................... 562/451

OTHER PUBLICATIONS

C. Ressler et al., J. Am. Chem. Soc. vol. 76, No. 12, 1954, pp. 3107-3109.
J. P. Tam et al., Tetrahedron Letters vol. 22, No. 28, 1981, pp. 2851-2854.

*Primary Examiner*—Johann Richter
*Attorney, Agent, or Firm*—Finnegan, Henderson, Farabow, Garrett and Dunner

[57] ABSTRACT

The invention relates to new compounds of the formula

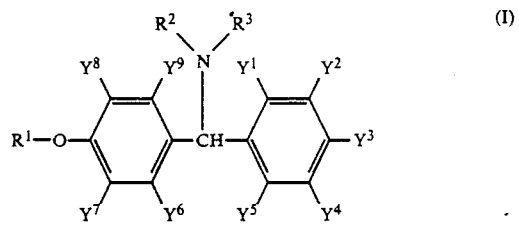

in which $R^1$ denotes $(C_1-C_8)$-alkyl, $R^2$ denotes an amino acid residue which is protected with a urethane protective group which can be eliminated with weak acid or base, or denotes an amino protective group which can be eliminated with weak acid or base, $R^3$ denotes hydrogen or $(C_1-C_4)$-alkyl, and $Y^1-Y^9$ denote identical or different radicals hydrogen, $(C_1-C_4)$-alkyl, $(C_1-C_4)$-alkoxy or $-O-(CH_2)_n-COOH$ (with n=1 to 6), with one of these radicals being $-O-(CH_2)_n-COOH$, or $Y^1$, $Y^2$ and $Y^5-Y^9$ denote identical or different radicals hydrogen, $(C_1-C_4)$-alkyl or $(C_1-C_4)$-alkoxy, $Y^3$ denotes hydrogen or $(C_1-C_8)$-alkoxy and $Y^4$ denotes $-(CH_2)_n-COOH$ or $-NH-CO-(CH_2)_n-COOH$ (with n=1 to 6).

Processes for the preparation thereof and the synthesis of peptide amides by a solid-phase method using these new compounds (spacers) are described.

5 Claims, No Drawings

ACID-LABILE ANCHOR GROUPS FOR THE SYNTHESIS OF PEPTIDE AMIDES BY A SOLID-PHASE METHOD

DESCRIPTION

The invention relates to new spacers and to processes for the preparation thereof, as well as to the synthesis of peptide amides by a solid-phase method using these acid-labile anchor groups.

Generally used for the preparation of peptide amides by solid-phase synthesis are benzhydrylamine- or methylbenzhydrylamine-resins as are described, for example, by J.P. Tam et al., Tetrahedron Lett. 22, 2851 (1981). Another method comprises the ammonolysis of carrier-bound peptide benzyl esters (C. Ressler et al., J. Am. Chem. Soc. 76, 3107 (1954)). Both methods are characterized by the strong acid (liquid hydrogen fluoride or trifluoromethanesulfonic acid) necessary for elimination of the spacer, by side reactions or by incomplete elimination.

Hence the invention has the object of finding new spacers which allow milder and better elimination of peptide amides from the support resin.

This object is achieved according to the invention by the compounds of the general formula I

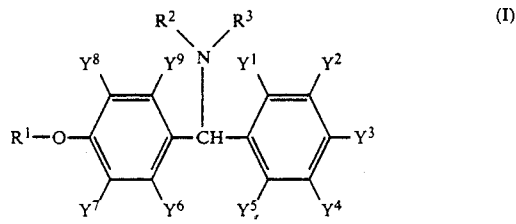

in which $R^1$ denotes $(C_1-C_8)$-alkyl, $R^2$ denotes an amino acid residue which is protected with a urethane protective group which can be eliminated with weak acid or base, or denotes an amino protective group which can be eliminated with weak acid or base, $R^3$ denotes hydrogen or $(C_1-C_4)$-alkyl, $Y^1$, $Y^2$, $Y^3$, $Y^4$, $Y^5$, $Y^6$, $Y^7$, $Y^8$ and $Y^9$ denote hydrogen, $(C_1-C_4)$-alkyl, $(C_1-C_4)$-alkoxy or —O—$(CH_2)_n$—COOH, where the radicals can be identical or different but one radical is —O—$(CH_2)_n$—COOH, or $Y^1$, $Y^2$, $Y^5$, $Y^6$, $Y^7$, $Y^8$ and $Y^9$ denote hydrogen, $(C_1-C_4)$-alkyl or $(C_1-C_4)$-alkoxy, where the radicals can be identical or different, $Y^3$ denotes $(C_1-C_8)$-alkoxy or hydrogen and $Y^4$ denotes —$(CH_2)_n$—COOH or —NH—CO—$(CH_2)_n$—COOH, and n denotes an integer from 1 to 6.

Preferred compounds of the general formula I are those in which $R^1$ is methyl, and n is an integer from 1 to 3.

Likewise preferred are compounds of this general formula I in which $R^2$ denotes an amino acid residue which is protected with Fmoc, or denotes a urethane protective H group — especially Fmoc — and $R^3$ denotes hydrogen.

Furthermore, the radicals $Y^1$–$Y^9$ particularly represent methyl or methoxy, with, however, one radical being —O—$(CH_2)_n$—COOH and at least 4 of these radicals being hydrogen, or the radicals $Y^1$, $Y^2$ and $Y^5$–$Y^9$ represent methyl or methoxy, with, however, at least 4 of these radicals being hydrogen, $Y^3$ represents methoxy, and $Y^4$ represents —$(CH_2)_n$—COOH. One radical $Y^1$, $Y^3$, $Y^5$, $Y^7$ or $Y^8$ preferably represents —O—$(CH_2)_n$—COOH. In compounds in which $Y^4$ denotes —$(CH_2)_n$—COOH, $Y^3$ is $(C_1-C_4)$-alkoxy, especially methoxy, and n=2; if $Y^4$ represents —NH—CO—$(CH_2)_n$—COOH, $Y^1$ and $Y^3$ preferably are methoxy and n=2. Alkyl and alkoxy can be straight-chain or branched.

$R^2$ represents a protective group which is base-labile or labile to weak acids, such as, for example, urethane protective groups such as Fmoc, Ddz, Bpoc, Msc, Peoc, Pse and Tse, preferably Fmoc (see, for example, Hubbuch, Kontakte (Merck) 1979, No. 3, pages 14–23) or represents the residue of an amino acid, preferably of an α-amino acid, which, if chiral, can be in the D or L form. Preference is given to residues of naturally occurring amino acids and the enantiomers, homologs, derivatives and simple metabolites thereof (cf., for example, Wunsch et al., Houben-Weyl 15/1 and 2, Stuttgart, Thieme 1974). Thus, suitable examples are:

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, Cyta, Daad, Dab, Dadd, Dap, Dapm, Dasu, Djen, Dpa, Dtc, Fel, Gln, Glu, Gly, Guv, hCys, His, hSer, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val and the residues of the corresponding enantiomeric D-amino acids.

Functional groups in the side chains of the said amino acid residues can be in protected form. Suitable protective groups are described by Hubbuch, Kontakte (Merck) 1979, No. 3, pages 14–23, and by Bullesbach, Kontakte (Merck) 1980, No. 1, pages 23–35.

The invention also relates to a process for the preparation of the compounds of the formula I, which comprises a) reacting a compound of the formula II

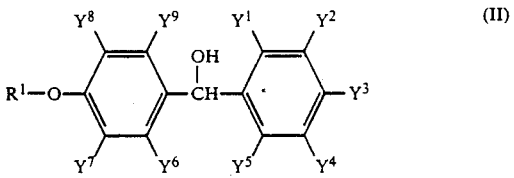

in which $R^1$ denotes $(C_1-C_8)$-alkyl, $Y^1$, $Y^2$, $Y^3$, $Y^4$, $Y^5$, $Y^6$, $Y^7$, $Y^8$ and $Y^9$ denote hydrogen, $(C_1-C_4)$-alkyl, $(C_1-C_4)$-alkoxy or —O—$(CH_2)_n$—COOH, where the radicals can be identical or different but one radical is —O—$(CH_2)_n$—COOH, or $Y^1$, $Y^2$, $Y^5$, $Y^6$, $Y^7$, $Y^8$ and $Y^9$ denote hydrogen, $(C_1-C_4)$-alkyl or $(C_1-C_4)$-alkoxy, where the radicals can be identical or different, $Y^3$ denotes $(C_1-C_8)$-alkoxy or hydrogen and $Y^4$ denotes —$(CH_2)_n$—COOH or —NH—CO—$(CH_2)_n$—COOH, and n denotes an integer from 1 to 6, with a compound of the formula III

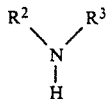  (III)

in which
R[2] denotes an amino acid residue which is protected with a urethane protective group which can be eliminated with weak acid or base, or denotes an amino protective group which can be eliminated with weak acid or base,
R[3] denotes hydrogen or ($C_1$-$C_4$)-alkyl, or
b) reacting a compound of the formula IV

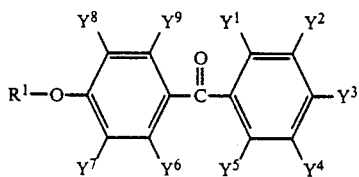  (IV)

with hydroxylamine to give a compound of the formula V

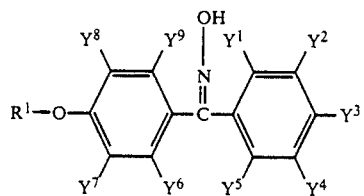  (V)

in which $R^1$, $Y^1$, $Y^2$, $Y^3$, $Y^4$, $Y^5$, $Y^6$, $Y^7$, $Y^8$ and $Y^9$ are as defined above,
subsequently reducing the oxime to the amine, preferably with zinc in glacial acetic acid or with Zn in ammoniacal ethanol (S. Gaehde, G. Matsueda, Int. J. Peptide Protein Res. 18, 451 (1981)) and, where appropriate, converting the amine by suitable reagents, such as, for example, chloroformic acid derivatives or carbonic acid derivatives, into compounds of the formula I in which $R^2$ denotes an amino protective group which can be eliminated by weak acid or base, and $R^3$ denotes hydrogen.

The reaction of a compound of the formula II with a compound of the formula III is preferably carried out in a polar protic solvent such as, for example, acetic acid at a temperature between 0° C. and the boiling point of the reaction mixture.

Compounds of the formula II are obtained, for example by reduction of benzophenone derivatives of the formula IV

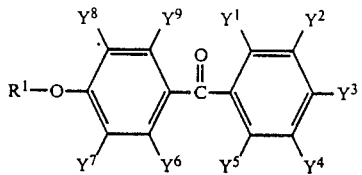  (IV)

in which $R^1$, $Y^1$, $Y^2$, $Y^3$, $Y^4$, $Y^5$, $Y^6$, $Y^7$, and $Y^9$ are as defined above, with suitable reducing agents, i.e. selective for the keto group, such as, for example, sodium borohydride.

Benzophenone derivatives of the formula IV are obtained
a) by reaction of benzophenones of the formula IV in which $R^1$ is as defined above, and $Y^1$, $Y^2$, $Y^3$, $Y^4$, $Y^5$, $Y^6$, $Y^7$, $Y^8$ and $Y^9$ denote hydrogen, ($C_1$-$C_4$)-alkyl or ($C_1$-$C_4$)-alkoxy, and one of the radicals $Y^1$-$Y^9$ denotes hydroxyl, with ω-halogeno fatty acids of the formula VI

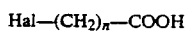  (VI)

in which Hal denotes halogen and n is as defined above, or esters thereof, followed, in the case of the esters, by alkaline hydrolysis of the ester group, for example with sodium hydroxide solution (M. Prashad et al., Indian J. Chem. 17B, 496–498 (1979)),
b) for example by reaction of benzoyl chlorides of the formula VII

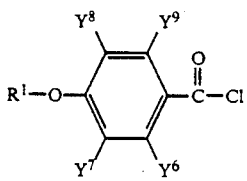  (VII)

with ω-phenoxyalkanoic acids of the formula VIII

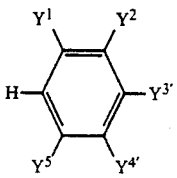  (VIII)

in which $R^1$, $Y^1$, $Y^2$, $Y^5$, $Y^6$, $Y^7$, $Y^8$ and $Y^9$ are as defined under a), $Y^{3'}$ represents —O—$(CH_2)_n$—$COOR^4$ and $Y^{4'}$ is defined as $Y^4$ under a), or $Y^{3'}$ is defined as $Y^3$ under a) and $Y^{4'}$ represents —$(CH_2)_n$—$COOR^4$, n is as defined under a) and $R^4$ denotes ($C_1$-$C_8$)-alkyl, preferably methyl or ethyl, by use of a Lewis catalyst such as, for example, aluminum trichloride or titanium tetrachloride (Organikum, 13th edition, page 354 (1974)), or
c) by reaction of the appropriate benzoyl chlorides of the formula VII with appropriately substituted phenols of the formula.IX to give the corresponding phenyl esters of the formula X

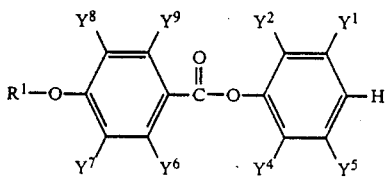  (X)

subsequent Fries rearrangement with Lewis acids such as, for example, titanium tetrachloride (R. Martin et al., Monatsh. Chemie 110, 1057–1066 (1979)) and then reaction with ω-halogeno fatty acids of the formula VI in which Hal and n are as defined above.

Compounds of the formula VIII in which $Y^{3'}$ denotes hydrogen or ($C_1$-$C_8$)-alkoxy and $Y^{4'}$ denotes —$(CH_2)_n$—$COOR^4$ are obtained, for example, by reaction of the appropriate benzaldehydes, in which $Y^{4'}$ represents CHO, with malonic monoesters in pyridine/piperidine to give the corresponding cinnamic esters, followed by hydrogenation. In this case, compounds of the formula VIII with n = 2 are obtained. It is likewise possible to react the appropriate benzaldehydes with halogenoacetic esters in the presence of zinc, to dehydrate to give the cinnamic esters, and subsequently to hydrogenate.

Compounds of the formula VIII in which $Y^{3'}$ represents $-O-(CH_2)_n-COOR^4$ and $Y^{4'}$ represents $Y^4$ are prepared by reaction of the appropriate phenols of the formula IX

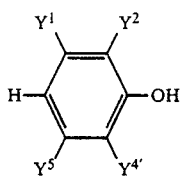 (IX)

with the appropriate ω-halogenoalkanoic esters, for example with sodium hydride in dimethylformamide (DMF) or potassium carbonate in acetone.

It is also possible analogously to prepare the compounds of the formulae VII, VIII, IX and X corresponding to the general formula I.

The invention also relates to the use of a compound of the formula I in the solid-phase synthesis of compounds of the formula XI $$P-R^2-NH-R^3 \qquad (XI)$$

in which P represents a peptide residue composed of $q \leq p+1$ α-amino acids, $R^2$ denotes an amino acid residue which is protected with a urethane group which can be eliminated with weak acid or base, or denotes an amino protective group which can be eliminated with weak acid or base, and $R^3$ is as defined above, as well as to a process for the preparation of a peptide of the formula XI, in which P, $R^2$ and $R^3$ are as defined above, by solid-phase synthesis, which comprises coupling a compound of the formula I, using coupling reagents customary in peptide chemistry, via the $-O-(CH_2)_n-COOH$, $-NH-CO-(CH_2)_n-COOH$ or $-(CH_2)_n-COOH$ group to a resin, eliminating the protective group of the amino acid residue $R^2$ or the protective group $R^2$, coupling on stepwise q-p α-amino acids which are temporarily protected by amino protective groups which are base-labile or labile to weak acids and are, where appropriate, in the form of their activated derivatives, and, after synthesis is complete, liberating the peptide of the formula XI from the resin by treatment with a moderately strong acid, with temporarily introduced side-chain protective groups being eliminated again simultaneously or by suitable measures subsequent thereto.

If necessary to prevent side reactions or for the synthesis of specific peptides, the functional groups in the side chain of amino acids are additionally protected by suitable protective groups (see, for example, T. W. Greene, "Protective Groups in Organic Synthesis", New York, John Wiley & Sons, 1981), those primarily used being Arg(Tos), Arg(Mts), Arg(Mtr), Asp(OBzl), Asp(OBut), Cys(4-MeBzl), Cys(Acm), Cys(SBut), Glu(OBzl), Glu(OBut), His(Tos), His(Fmoc), His(Dnp), His(Trt), Lys(Cl-2), Lys(Boc), Met(O), Ser(Bzl), Ser(But), Thr(Bzl) and Thr(But).

The resins used as support material are commercially available or prepared by the user, such as, for example, alkoxybenzyl alcohol resins, aminomethyl resins or benzhydrylamino resins. Aminomethyl-, benzhydrylamino-(BHA) and methylbenzhydrylamino-(MBHA) resins are preferred. The loading is determined by amino acid analysis and/or elemental analysis.

It is possible to use as coupling reagents for the compound of the formula I and the other amino acid derivatives all the possible activating reagents used in peptide synthesis, see, for example, Houben-Weyl, Methoden der organischen Chemie (Methods of Organic Chemistry), Volume 15/2, but especially carbodiimides such as, for example, N,N'-dicyclohexylcarbodiimide, N,N'-diisopropylcarbodiimide or N-ethyl-N'-(3-dimethylaminopropyl)carbodiimide. This coupling can be carried out directly by addition of amino acid derivative with the activating reagent and, where appropriate, an additive suppressing racemization, such as, for example, 4-dimethylaminopyridine, 1-hydroxybenzotriazole (HOBt) (W. König, R. Geiger, Chem. Ber. 103, 708 (1970)) or 3-hydroxy-4-oxo-3,4-dihydrobenzotriazine (HOObt) (W. König, R. Geiger, Chem. Ber. 103, 2054 (1970)) to the resin, or else the preactivation of the amino acid derivative as symmetric anhydride or HOBt or HOObt ester can be carried out separately, and the solution of the activated species in a suitable solvent can be added to the peptide-resin which is ready for coupling.

The coupling and activation of the compound of the formula I and of the amino acid derivatives using one of the abovementioned activating reagents can be carried out in dimethylformamide or methylene chloride or a mixture of the two. The activated amino acid derivative is normally used in a 1.5- to 4-fold excess. In cases where incomplete coupling occurs, the coupling reaction is repeated without previously carrying out the deblocking of the α-amino group of the peptide-resin which is necessary for coupling the next amino acid in the sequence.

It is possible to check that the coupling reaction has taken place successfully by means of the ninhydrin reaction as described, for example, by E. Kaiser et al. Anal. Biochem. 34 595 (1970). The synthesis can also be carried out automatically, for example using an Applied Biosystems model 430A peptide synthesizer, it being possible to use either the synthesis programs provided by the manufacturer of the apparatus or else those constructed by the users themselves. The latter are employed especially when amino acid derivatives protected with the Fmoc group are used.

The peptide amides are eliminated from the resin by treatment with the moderately strong acids customarily used in peptide synthesis (for example trifluoroacetic acid), with addition, as cation traps, of substances such as phenol, cresol, thiocresol, anisole, thioanisole, ethanedithiol, dimethyl sulfide, ethyl methyl sulfide or similar cation traps customary in solid-phase synthesis, singly or a mixture of two or more of these auxiliaries. The trifluoroacetic acid can also be used for this diluted with suitable solvents such as, for example, methylene chloride. The elimination of the spacer from the resin takes place at the same time as the elimination of the side-chain protective groups.

The crude peptides obtained in this way are purified by chromatography on ®Sephadex, ion exchanger resins or HPLC.

The examples which follow serve to illustrate the present invention without intending to restrict it to them.

EXAMPLE 1

Methyl 4-phenoxybutyrate 16 ml of thionyl chloride are added dropwise to 160 ml of ice-cooled dry methanol, and then 36 g of phenoxybutyric acid are added in portions. The mixture is subsequently stirred at 40° C. for one hour. The excess methanol is then removed in vacuo, and the residue which remains is recrystallized from petroleum ether (cooling to −20° C.).

Yield: 34.5 g, melting point: 25.5°–26.5° C.

EXAMPLE 2

Methyl 4-[4-(4-methoxybenzoyl)phenoxy]butyrate 25.6 g of anhydrous aluminum trichloride are suspended in 64 ml of 1,2-dichloroethane, and 28.6 g of 4-methoxybenzoyl chloride are added. Then, while stirring vigorously, 31 g of methyl 4-phenoxybutyrate are slowly added. The reaction mixture is subsequently stirred at 50° C. for 4 hours, allowed to cool and poured into ice-water. The oily organic layer and the aqueous phase are separated, the organic phase is washed with water, and a little methanol is added to induce crystallization. The product which has separated out is filtered off with suction and recrystallized from ethyl acetate.

Yield: 41 g, melting point: 117°–118° C.

EXAMPLE 3

4-[4-(4-Methoxybenzoyl)phenoxy]-butyric acid 41 g of methyl 4-[4-(4-methoxybenzoyl)phenoxy]butyrate from Example 2 are dissolved in 600 ml of dimethoxyethane/water 4:1, and 63 ml of 2N sodium hydroxide solution are added. The mixture is stirred at room temperature for 4 hours, then acidified to pH 3 with 3N hydrochloric acid, and the organic solvent is removed in vacuo. The acid which has separated out is filtered off and dried over phosphorus pentoxide in vacuo.

Yield: 38.7 g, melting point: 141°–142° C.

EXAMPLE 4

[4-(3-Carboxypropyloxy)phenyl]-4-methoxyphenylcarbinol 18.9 g of 4-[4-(4-methoxybenzoyl)phenoxy]butyric acid (Example 3) are dissolved in 600 ml of methanol at 40° C., and 60 ml of 1N sodium hydroxide solution and 3.4 g of sodium borohydride are added in portions. The mixture is subsequently stirred at 40° C. for one hour and then reduced to a small volume, and the pH is adjusted to 2.8 with 3N hydrochloric acid. The methanol is subsequently removed in a rotary evaporator, the aqueous mixture is extracted with ethyl acetate, and the organic solution is washed with saturated sodium chloride solution. Drying over sodium sulfate is followed by removal of the solvent. 18.2 g of an amorphous substance remain and are immediately reacted further. General procedure for the coupling of Fmoc-amide (9-fluorenylmethylcarbamate) onto carbinol derivatives 20 mmol of Fmoc-amide and 20 mmol of freshly prepared carbinol are dissolved in 50 ml of hot glacial acetic acid. Then 5 drops of concentrated sulfuric acid are added, and the mixture is stirred at room temperature or at 40° C. The progress of the reaction is checked by thin-layer chromatography. After the reaction is complete, the glacial acetic acid solution is poured onto ice-water, and the product which separates out is filtered off with suction and recrystallized.

EXAMPLE 5

N-Fmoc-[4-(3-carboxypropyloxy)phenyl]-4-methoxyphenyl methylamide

The [4-(3-carboxypropyloxy)phenyl]-4-methoxyphenylcarbinol prepared in Example 4 is reacted by the above procedure.

Yield: 91%, melting point: 186°–187° C.

Analysis: $C_{33}H_{31}NO_6$ calculated: C 73.73, H 5.81, N 2.61, found: C 73.6, H 6.0, N 2.6

EXAMPLE 6

N-Fmoc-[4-(3-carboxymethyloxy)phenyl]-4-methoxyphenylmethylamide

The [4-(3-carboxymethyloxy)phenyl]-4-methoxyphenylcarbinol described in German Patent Application P 37 11 866.8, Example 3, is reacted by the above procedure.

Yield: 60%, melting point: 176°–179° C.

Analysis: $C_{31}H_{27}NO_6$ calculated: C 73.1, H 5.3, N 2.75, found: C 73.3, H 5.3, N 2.95

EXAMPLE 7

Synthesis of

H-Leu-Gly-Gly-Gly-Gln-Gly-Lys-Val-Leu-Gly-NH₂ by use of the anchor described in Example 5. The synthesis was carried out in a Labotec peptide synthesizer.

Firstly, the protective group was removed, using trifluoroacetic acid in methylene chloride, from 1.5 g of Boc-Val-resin (loaded with 0.76 mmol/g). The resin was washed with dichloromethane and ethyldiisopropylamine and then again dichloromethane and was then dried. Subsequently 2.1 mmol of the anchor prepared in Example 5, together with 3.15 mmol of HOBt dissolved in 20 ml of dry DMF, were added to the resin and then 2.3 mmol of diisopropylcarbodiimide were added. The mixture was left, mixing slowly, to react at room temperature overnight. The completeness of the reaction was checked by the ninhydrin reaction (Kaiser test). The resin was then filtered off with suction and washed with DMF, and subsequently the peptide was synthesized on the resin (1 g of the resin prepared above was used for the synthesis), with the following steps being carried out cyclically.

Elimination of the Fmoc protective group with 20% piperidine in DMF

Washing of the resin with DMF

Coupling of the Fmoc-amino acid on, with in situ activation as HOBt ester using diisopropylcarbodiimide as activating reagent (1.5 mmol of amino acid, 2.25 mmol of HOBt, 1.6 mmol of diisopropylcarbodiimide).

If the coupling was incomplete (Kaiser test), the coupling step was repeated. The last amino acid used was Boc-Leu-OH.

After the synthesis was complete, the resin was washed with DMF and isopropanol and dried under high vacuum. Elimination was carried out with a mixture of 20 ml of trifluoroacetic acid/15 ml of dichloromethane/5 ml of thioanisole/0.5 ml of ethanedithiol at room temperature for a period of 2.5 hours. The mixture was then filtered with suction into diethyl ether, washing with 50% strength trifluoroacetic acid in dichloromethane. The crude peptide which separated out was filtered off with suction and washed three times with diethyl ether and dried under high vacuum.

Yield: 91% of crude peptide

Amino acid analysis: Gly 5.1; Glu 0.98; Leu 1.78; Val 0.81; Lys 1.01.

EXAMPLE 8

Ethyl 2,4-dimethoxycinnamate 83 g of 2,4-dimethoxybenzaldehyde and 66 g of monoethyl malonate are dissolved in 100 ml of dry pyridine and, after addition of 1 ml of piperidine and 40 g of molecular sieves, refluxed until evolution of $CO_2$ has ceased. The reaction mixture is cooled and then poured onto crushed ice, and the pH is adjusted to 1–2 with concentrated hydrochloric acid, while stirring. Stirring is continued for 20 minutes, and the product which has separated out is filtered off with suction, washed with 1 N hydrochloric acid and water and dried in a desiccator. Yield: 100.2 g, melting point 58° C.

EXAMPLE 9

Ethyl 2,4-dimethoxyhydrocinnamate 100.2 g of ethyl 2,4-dimethoxycinnamate are dissolved in 400 ml of methanol and hydrogenated with palladium/charcoal under atmospheric pressure. The catalyst is filtered off with suction, and the filtrate is concentrated in vacuo.

Yield: 94.7 g of yellowish oil

EXAMPLE 10

Ethyl 3-[2,4-dimethoxy-5-(4-methoxybenzoyl)phenyl]propionate 52 g of aluminum trichloride are suspended in 200 ml of 1,2-dichloroethane and cooled to 0° C. Then, at this temperature, 66.5 g of 4-methoxybenzoyl chloride are added dropwise, followed by 94.7 g of ethyl 2,4-dimethoxyhydrocinnamate in 30 ml of 1,2-dichloroethane. The mixture is then heated at 50° C. with exclusion of moisture until the reaction is complete. The reaction mixture is then poured onto ice-water, and the organic phase is separated off, diluted with 200 ml of methylene chloride and then extracted with sodium bicarbonate solution and water. It is dried over magnesium sulfate and concentrated. A gray-brown solid remains and is immediately reacted further.

Yield: 128.9 g, melting point 89° C.

EXAMPLE 11

3-[2,4-dimethoxy-5-(4-methoxybenzoyl)phenyl]propionic acid 55.8 g of ethyl 3-[2,4-dimethoxy-5-(4-methoxybenzoyl)=phenyl]propionate are mixed with 300 ml of 2N sodium hydroxide solution and 300 ml of dioxane and stirred overnight. The dioxane is then removed in vacuo, and the alkaline aqueous solution is extracted once with 100 ml of ethyl acetate. The aqueous phase is adjusted to pH 2 with concentrated hydrochloric acid, when part of the product separates out. The mixture is extracted three times with 200 ml of ethyl acetate each time, and the organic phase is washed with water, dried over sodium sulfate and concentrated. The residue is recrystallized from ethyl acetate/acetone/hexane.

Yield: 37 g, melting point 177°–180° C.

EXAMPLE 12

Methyl 2,4-dimethoxycinnamate

A mixture of 105.6 g of 2,4-dimethoxybenzaldehyde, 93.6 g of methyl potassium malonate, 200 ml of pyridine (dried over KOH), 1.2 ml of piperidine, 36 ml of acetic acid and 48 g of 3A molecular sieves is heated at 150° C. until evolution of $CO_2$ has ceased. The solution is poured onto ice while hot, and the mixture is acidified to pH 1–2 with concentrated hydrochloric acid and then stirred in the ice bath for 20 minutes. The precipitate is filtered off with suction, washed with 1N HCl and water and dried.

Yield: 113.8 g, melting point: 78° C.

EXAMPLE 13

2,4-Dimethoxycinnamic acid 180 ml of dry pyridine are placed in a 1 l three-necked flask with magnetic stirrer, reflux condenser and internal thermometer, and 124.9 g of malonic acid are dissolved therein by stirring. Then 166.18 g of 2,4-dimethoxybenzaldehyde are added in portions, during which the internal temperature falls to 25° C. 9.9 ml of dry piperidine are added to the resulting mixture, which is then slowly heated. The bath temperature is adjusted to 130° C. Evolution of $CO_2$ is complete after 1.5 hours, and the mixture boils at 107° C. The hot mixture is then poured onto 1 kg of ice. The mixture is acidified to pH 1 with concentrated HCl while stirring, and stirring is continued while cooling in ice for 20 minutes, and the precipitate is filtered off with suction. It is washed 3 times with 200 ml of each of 2N HCl and water and dried. The aldehyde which still remains is removed by suspending the precipitate in 600 ml of hot cyclohexane and again filtering with suction. The product is then washed with 100 ml of hot cyclohexane and dried in a desiccator. The aldehyde crystallizes out of the filtrate on cooling. Another possible purification comprises recrystallization from methanol/water. For this, the product is dissolved in the minimum amount of hot methanol, and water is added to opalescence. On cooling, the cinnamic acid separates out while the aldehyde remains in solution.

Yield: cinnamic acid 181.4 g (treated with cyclohexane), aldehyde 14.5 g (precipitated from cyclohexane).

Melting point: 182°–184° C.

EXAMPLE 14

Methyl 3-(2,4-dimethoxyphenyl)propionate 20.8 g of 2,4-dimethoxycinnamic acid are dissolved in a hot mixture of 500 ml of methanol and 100 ml of ethyl acetate and, after addition of 1 g of catalyst (10% Pd/C), hydrogenated under atmospheric pressure. The uptake of hydrogen ought to be complete after 3 hours. If the hydrogenation is incomplete, more fresh catalyst is added. After the reaction is complete, the catalyst is removed, the solution is concentrated to about 200 ml, 20 ml of an approx. 2.4 M methanolic hydrochloric acid solution are added, and the mixture is left to stand at room temperature for 2 days. The esterification is then complete. The methanol is removed in vacuo, the residue is taken up in 200 ml of ethyl acetate, and the organic phase is washed with $NaHCO_3$ solution and saturated NaCl solution (50 ml each 3 times), dried over Na$_2$SO$_4$ and concentrated.

Yield: 20.0 g of an oil

EXAMPLE 15

Methyl 3-(2,4-dimethoxyphenyl)propionate 113.8 g of methyl 2,4-dimethoxycinnamate are dissolved in 1.5 l of methanol while heating and are hydrogenated on 5 g of catalyst (10% Pd/C). The catalyst is removed by filtration and the filtrate is concentrated. 113 g of an oil remain and are immediately used in the subsequent Friedel-Crafts acylation.

Yield: 113 g of oil

EXAMPLE 16

Methyl 3-[2,4-dimethoxy-5-(4-methoxybenzoyl)phenyl]propionate 36.6 g of aluminum trichloride are suspended in 130 ml of 1,2-dichloroethane, and 42.65 g of 4-methoxybenzoyl chloride are added to the mixture which has been cooled to 0° C. Then, at this temperature, 56 g of methyl 3-(2,4-dimethoxyphenyl)propionate (Example 17) dissolved in 30 ml of 1,2-dichloroethane are added dropwise, and the mixture is then stirred at 50° C. with exclusion of moisture until the reaction is complete (about 36 hours). 200 ml of water are added to the cooled reaction mixture which is then diluted with 400 ml of CH$_2$Cl$_2$, extracted with bicarbonate and water, dried over sodium sulfate and concentrated. The residue is dissolved in diisopropyl ether and precipitated with hexane. Filtration with suction results in 62.1 g of the product, and a further 10.5 g from the mother liquor.

Yield: 72.6 g, melting point: 114°–117° C.

EXAMPLE 17

3-[2,4-dimethoxy-5-(4-methoxybenzoyl)phenyl]propionic acid 60.9 g of methyl 3-[2,4-dimethoxy-5-(4-methoxybenzoyl)phenyl]propionate are mixed with 300 ml of 2N sodium hydroxide solution and 300 ml of dioxane and stirred overnight. The dioxane is then removed in vacuo, and the alkaline aqueous solution is extracted once with 100 ml of ethyl acetate. The aqueous phase is adjusted to pH 2 with concentrated hydrochloric acid, when part of the product separates out. The mixture is extracted three times with 200 ml of ethyl acetate each time, and the organic phase is washed with water, dried over sodium sulfate and concentrated. The residue is recrystallized from ethyl acetate/acetone/hexane.

Yield: 51.3 g, melting point: 177°–180° C.

EXAMPLE 18

5-Carboxyethyl-2,4-dimethoxy-4'-methoxybenzophenone oxime 37 g of 3-[2,4-dimethoxy-5-(4-methoxybenzoyl)phenyl]propionic acid, 22.4 g of hydroxylamine hydrochloride and 21 g of sodium acetate (anhydrous) are added to 300 ml of absolute ethanol, and the mixture is refluxed with exclusion of moisture for 24 hours. Insolubles are removed by suction, the filtrate is concentrated, and water is added to the residue. The pH is then adjusted to 2 with 1N hydrochloric acid, and the mixture is extracted with ethyl acetate. The organic phase is washed with water, dried over magnesium sulfate and concentrated. The residue is recrystallized from ethyl acetate/hexane.

Yield: 34.3 g, melting point 124°–128° C.

EXAMPLE 19

N-(9-fluorenylmethoxycarbonyl)-(5-carboxyethyl-2,4-dimethoxyphenyl)-4-methoxyphenylmethylamine 34 g of 5-carboxyethyl-2,4-dimethoxy-4'-methoxybenzophenone oxime are added to a mixture of 100 ml of ethanol and 500 ml of 25% strength ammonia solution, then 29.5 g of zinc powder are added, and the mixture is stirred at 50° C. overnight. A further 30 g of zinc and 260 ml of 25% strength ammonia are then added, and the mixture is stirred at 50° C. for a further 24 hours. The zinc is removed by filtration with suction while hot, and the ethanol is removed in vacuo. The cooled aqueous phase is neutralized with concentrated hydrochloric acid and extracted once with ethyl acetate.

The resulting amine is not isolated but the aqueous solution is immediately reacted further. For this, the solution is adjusted to pH 8 with solid sodium bicarbonate and diluted with 250 ml of tetrahydrofuran, and 31 g of 9-fluorenylmethyl succinimidyl carbonate are added and the mixture is stirred overnight. Insolubles are then removed by filtration, the tetrahydrofuran is removed in vacuo, and the aqueous phase is acidified with 1N sulfuric acid. It is extracted with ethyl acetate, and the organic phase is washed with saturated sodium chloride solution, dried over magnesium sulfate and concentrated. The residue is dissolved in hot ethyl acetate and, after brief cooling, ether is added, followed by hexane to opalescence. The mixture is left to stand in a cold room overnight, and the product which has separated out is filtered off with suction and crystallized once again in the manner described.

Yield: 37.1 g, melting point 149°–151° C.

Alternatively, the product can also be obtained by catalytic hydrogenation of the oxime on 10% palladium/charcoal in ammoniacal ethanol, followed by reaction with 9-fluorenylmethyl succinimidyl carbonate as described above.

EXAMPLE 20

Preparation of the Fmoc-amide-resin 30.7 g of aminomethylated polystyrene resin (loaded with 1.04 mmol of NH2/g) and 28 g (49.5 mmol) of N-(9-fluorenylmethoxycarbonyl)-(5-carboxyethyl-2,4-dimethoxyphenyl)-4'-methoxyphenylmethylamine were suspended in a mixture of 210 ml of dimethylformamide and 90 ml of dichloromethane. 6.4 g of HOObt and 23 ml of diisopropylcarbodiimide were added and the mixture was shaken overnight. After this the reaction was complete, and the resin was filtered off with suction and washed with DMF, DCM and MTB ether. Drying under high vacuum yielded 46.5 g of product loaded with 0.57 mmol/g (determined by elemental analysis) or 0.54 mmol/g (determined by test elimination of Fmoc-NH$_2$ and quantification by HPLC).

PEPTIDE SYNTHESIS

The following reaction scheme was used for the peptide synthesis:

Elimination of the Fmoc protective group with 20% piperidine in DMF, washing with NMP, coupling on of the subsequent Fmoc-amino acid as the HOObt ester dissolved in NMP or as the HOObt ester preactivated in situ with diisopropylcarbodiimide in DMF or NMP, and washing with NMP. This cycle was run through until the peptide had been synthesized on the resin. The efficiency of the coupling can be followed by means of the ninhydrin test.

EXAMPLE 21 pGlu-His-Trp-Ser-Tyr-Gly-Leu-Arg-Pro-Gly-NH$_2$

The peptide was synthesized on 877 mg of the resin prepared above. The crude peptide was eliminated using TFA/ethanedithiol/thioanisole 90/5/5 in 1 hour at room temperature. 450 mg of crude product were obtained and were identical to an authentic sample by HPLC.

FAB MS (Tg, TFA): 1182 (M+H$^+$)

EXAMPLE 22

H-Leu-Leu-Gln-Gly-Leu-Val-NH$_2$

The peptide was synthesized on 877 mg of the resin prepared above. The crude peptide was eliminated using TFA/water 95/5 in 1 hour at room temperature. 38 mg of crude product were obtained from 100 mg of resin and were identical to an authentic sample.

FAB MS (3-NBA): 641 (M+H$^+$)

EXAMPLE 23

H-Ile-Pro-Glu-Tyr-Leu-Gln-OH

This peptide was synthesized on 877 mg of resin as described above. The first amino acid coupled on was Fmoc-Glu-OtBu. This results, after elimination from the resin with 95% TFA/water, in the peptide with C-terminal glutamine.

We claim:

1. A compound of the formula I

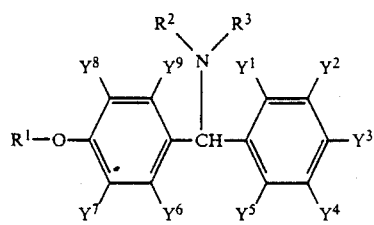

in which

R$^1$ denotes (C$_1$–C$_6$)-alkyl,

R$^2$ denotes an amino protective group which can be eliminated with weak acid or base, R$^3$ denotes hydrogen or (C$_1$–C$_4$)-alkyl, Y$^1$, Y$^2$, Y$^3$, Y$^4$, Y$^5$, Y$^6$, Y$^7$, Y$^8$ and Y$^9$ denote hydrogen, (C$_1$–C$_4$)-alkyl, (C$_1$–C$_4$)-alkoxy or —O—(CH$_2$)$_n$—COOH, where the radicals can be identical or different but one radical is —O—(CH$_2$)$_n$—COOH, or Y$^1$, Y$^2$, Y$^5$, Y$^6$, Y$^7$, Y$^8$ and Y$^9$ denote hydrogen, (C$_1$–C$_4$)-alkyl or (C$_1$–C$_4$)-alkoxy, where the radicals can be identical or different, Y$^3$ denotes (C$_1$–C$_8$)-alkoxy or hydrogen and Y$^4$ denotes —(CH$_2$)$_n$—COOH or —NH—CO—(CH$_2$)$_n$—COOH, and n denotes an integer from 1 to 6.

2. A compound of the formula I as claimed in claim 1, in which R$^1$ is methyl and n is an integer from 1 to 3.

3. A compound of the formula I as claimed in claim 1, in which the radicals Y$^1$–Y$^9$ represent methyl or methoxy, with, however, one radical being —O—(CH$_2$)$_n$—COOH and at least 4 of these radicals being hydrogen, or the radicals Y$^1$, Y$^2$ and Y$^5$–Y$^9$ represent methyl or methoxy, with, however, at least 4 of these radicals being hydrogen, Y$^3$ represents methoxy and Y$^4$ represents —(CH$_2$)$_n$—COOH.

4. A compound of the formula I as claimed in claim 1, in which one radical Y$^1$, Y$^3$, Y$^5$, Y$^7$ or Y$^8$ represents —O—(CH$_2$)$_n$—COOH.

5. A compound of the formula I as claimed in claim 1, in which Y$^4$ denotes —(CH$_2$)$_n$—COOH, Y$^3$ is (C$_1$–C$_4$)-alkoxy and n is 2, or Y$^4$ represents —NH—CO—(CH$_2$)$_n$—COOH, Y$^1$ and Y$^3$ denote methoxy and n=2.

* * * * *

UNITED STATES PATENT AND TRADEMARK OFFICE
CERTIFICATE OF CORRECTION

PATENT NO. : 5,124,478

DATED : June 23, 1992

INVENTOR(S) : Gerhard Breipohl et al.

It is certified that error appears in the above-identified patent and that said Letters Patent is hereby corrected as shown below:

Claim 1, column 14, line 12, change "$(C_1-C_6)$-alkyl)" to --$(C_1-C_8)$-alkyl.

Signed and Sealed this

Twenty-eighth Day of September, 1993

Attest:

BRUCE LEHMAN

*Attesting Officer*   *Commissioner of Patents and Trademarks*